United States Patent [19]

Marchlinski et al.

[11] Patent Number: 5,447,529
[45] Date of Patent: Sep. 5, 1995

[54] METHOD OF USING ENDOCARDIAL IMPEDANCE FOR DETERMINING ELECTRODE-TISSUE CONTACT, APPROPRIATE SITES FOR ARRHYTHMIA ABLATION AND TISSUE HEATING DURING ABLATION

[75] Inventors: Francis E. Marchlinski, Bala Cynwyd; David S. Schwartzman, Philadelphia, both of Pa.; Mark S. Mirotznik, Silver Spring, Md.; Kenneth R. Foster, Haverford, Pa.; Charles D. Gottleb, Wynnewood, Pa.; Isaac Chang, Philadelphia, Pa.

[73] Assignees: Philadelphia Heart Institute; The Trustees of the University of Pennsylvania, both of Philadelphia, Pa.; Catholic University of America, Washington, D.C.

[21] Appl. No.: 188,514

[22] Filed: Jan. 28, 1994

[51] Int. Cl.⁶ .................... A61B 17/39; A61N 1/05
[52] U.S. Cl. .................... 607/99; 128/739; 128/642; 128/695 R; 128/713; 607/122
[58] Field of Search ............ 128/637, 642, 662.06, 128/670, 692, 701, 713, 654, 672, 695 R, 734, 693; 606/41; 607/41, 99

[56] References Cited

U.S. PATENT DOCUMENTS

| | | | |
|---|---|---|---|
| 4,380,237 | 4/1983 | Newbower | 128/693 |
| 4,674,518 | 6/1987 | Salo | 128/695 |
| 4,852,580 | 8/1989 | Wood | 128/693 |
| 5,058,583 | 10/1991 | Geddes et al. | 128/419 |
| 5,092,339 | 3/1992 | Geddes et al. | 128/692 |
| 5,195,968 | 3/1993 | Lundquist et al. | 604/95 |
| 5,197,467 | 3/1993 | Stenhaus et al. | 128/419 |
| 5,224,475 | 7/1993 | Berg et al. | 128/419 |
| 5,239,999 | 8/1993 | Imran | 128/642 |
| 5,246,008 | 9/1993 | Mueller | 128/695 |
| 5,282,840 | 2/1994 | Hudrlik | 607/28 |
| 5,334,193 | 8/1994 | Nardella | 606/41 |
| 5,341,807 | 8/1994 | Nardella | 606/41 |

OTHER PUBLICATIONS

Myocardial Electrical Impedance Mapping of Ischemic Sheep Hearts and Healing Aneurysms–Circulation, vol. 87, pp. 188–207 (1993).

*Primary Examiner*—Lee S. Cohen
*Assistant Examiner*—Stephen Huang
*Attorney, Agent, or Firm*—Michael F. Petock

[57] ABSTRACT

A method of locating infarcted myocardial tissue in a beating heart includes the step of inserting an impedance measuring tip of a catheter into the chamber of the beating heart, particularly the left or right ventricle, and measuring the impedance of the endocardium at various locations within the chamber of the beating heart. The values measured are compared to impedance values with a predetermined range of values to identify an infarcted area of myocardium and distinguish such area from normal myocardium. The measurements are also compared to a range of values for an infarction border zone. In accordance with the invention, the infarction border zone may be located. The infarction border zone is a significant source of arrhythmia, and particularly of ventricular tachycardia. Further, in accordance with the methods of the present invention, the risk of arrhythmia in a beating heart may be substantially reduced or eliminated by ablating endocardium within the infarction border zone utilizing the same catheter tip. Impedance measurements may also be utilized to assess the adequacy of the electrode-tissue contact, particularly in a fluid filled body organ or cavity. Further, the effectiveness of the ablation of the tissue may be determined by determining the degree of heating of the tissue by measuring the change in impedance in the area of ablation.

16 Claims, 2 Drawing Sheets

METHOD OF USING ENDOCARDIAL IMPEDANCE FOR DETERMINING ELECTRODE-TISSUE CONTACT, APPROPRIATE SITES FOR ARRHYTHMIA ABLATION AND TISSUE HEATING DURING ABLATION

FIELD OF THE INVENTION

The present invention relates to methods of using measurements of endocardial impedance for the determination of arrhythmiogenic sites for catheter ablation, assessing catheter-tissue contact and methods of confirming tissue ablation during and after energy delivery. More particularly, the present invention relates to methods of determining an infarction border zone in a beating, post-myocardial infarcted heart, using impedance measurements to insure adequate catheter-tissue contact and measuring the impedance as a confirmation of heating of the tissue during the ablation process, the later two being useful on various tissues and organs and not limited to cardiac applications.

BACKGROUND OF THE INVENTION

It has been known for some time that one of the long term sequelae of a myocardial infarction is the generation of arrhythmias, such as tachycardia which may result in fibrillation of the heart and sudden death. Accordingly, for some time, efforts have been directed at reducing the risk of such arrhythmias. For years, attempts have been made to reduce the risk of arrhythmia by pharmacological treatment.

More recently, a surgical approach to the eradication of tissue which generates ventricular tachycardia has been utilized which renders the target endocardium and sub-endocardium electrically inert or surgically removes it. This surgical procedure has been demonstrated to be highly effective, however perioperative mortality is high due to left ventricular failure, and only a small percentage of patients with ventricular tachycardia are candidates for this procedure.

Most recently, attempts to eradicate arrhythmic tissue have included the application of radiofrequency energy via an electrode mounted on a catheter tip, known as "catheter ablation". For example, see U.S. Pat. No. 5,239,999—Imran.

There are significant problems with the catheter ablation process as previously practiced, including the inability to judge adequate contact between the ablating electrode and the target endocardium. Another problem is the inability to locate appropriate targets for ablation. Still another problem is the inability to determine when the radiofrequency energy applied via an electrode mounted on a catheter successfully ablates the tissue intended to be ablated.

In the past, techniques to localize the endocardial origin of ventricular tachycardia in the setting of chronic myocardial infarction have utilized only electrogram characteristics. These techniques have included sinus rhythm mapping, activation mapping, pace-mapping and entrainment mapping. These techniques have poor specificity for localization of the site of origin of ventricular tachycardia. In addition, to properly perform some of these techniques, long periods of sustained tachycardia are necessary, often placing a significant hemodynamic burden on the patient.

SUMMARY OF THE INVENTION

The present invention is directed to a method of locating infarcted myocardial tissue in a beating heart which includes the step of inserting an impedance measuring tip of a catheter into a chamber of a beating heart, measuring the impedance of the endocardium at various locations within the chamber of the beating heart and comparing the measured impedance values with a predetermined range of values and/or assessing differences in impedance ranges to identify an infarcted area of myocardium and distinguish such area from normal myocardium.

It has been found that there is a two fold decrease in impedance measured on the endocardium of infarcted tissue as contrasted to normal endocardium. Ranges of values may be tabulated and impedance measurements compared with these values. Alternatively, measurements may be taken on various surfaces of the endocardium and compared with each other to determine infarcted areas as well as border zones between infarcted endocardium and normal endocardium. The border zone between normal and infarcted endocardium, particularly in the ventricles, is often a source of the generation of an arrhythmia such as ventricular tachycardia.

In accordance with the present invention, a method of reducing the risk of arrhythmia in a beating heart utilizes the step of inserting a tip of a catheter into a chamber of a beating heart wherein the tip is adapted for both impedance measurement and ablation. The impedance of the endocardium at various locations within the chamber of the beating heart is measured using the tip of the catheter in the measuring mode of operation. Once the border zone between normal and infarcted endocardium, referred to herein as the infarction border zone is located, sufficient energy is applied to the tip of the catheter to ablate endocardium in the infarction border zone.

Further in accordance with the present invention, a method is provided of assessing the adequacy of electrode-tissue contact in a fluid filled organ which includes the steps of inserting an impedance measuring electrode mounted on a catheter into a desired portion of a fluid filled organ and determining whether the electrode is in contact with the organ tissue based on the impedance value. In a presently preferred embodiment, the method is utilized to assess the adequacy of electrode contact with the endocardium in a catheter ablation process by first measuring the impedance value when the electrode is in blood, such as in the aorta outside of the heart to determine a base line value and detecting the change in impedance when the electrode comes in contact with the endocardium.

Further, in accordance with the present invention, a method of assessing the effectiveness of tissue ablation utilizes the steps of measuring the impedance of tissue at or around the area of tissue to be ablated at body temperature and measuring the impedance of the tissue in the area being ablated during the application of ablation energy in order to assess the degree of heating of the tissue. It has been found that tissue impedance declines substantially proportionally to tissue temperature during the ablation process. Accordingly, in cardiac catheter ablation, the effectiveness of the ablation of the endocardium may be monitored to insure, by measuring the change in impedance, that sufficient heating of the endocardium has taken place to insure tissue ablation adequate to eliminate the arrhythmiogenic site.

The terms impedance or electrical impedance as utilized herein are intended in their broadest sense, that is including the resistive component and/or inductive reactance and/or capacitive reactance, including the condition wherein the capacitive and inductive reactances may cancel or are nonexistent leaving only the resistive component as the impedance. In a co-pending application filed the same day as this application, application Ser. No. 08/138,142, filed by some of the same applicants herein and entitled *Systems and Methods for Examining the Electrical Characteristics of Cardiac Tissue*, the term "E-Characteristic" has been utilized in connection with such impedance and resistance values.

BRIEF DESCRIPTION OF THE DRAWINGS

For the purpose of illustrating the invention, there shown in the drawings forms which are presently preferred; it being understood, however, that this invention is not limited to the precise arrangements and instrumentalities shown.

DETAILED DESCRIPTION OF THE PREFERRED EMBODIMENTS

A myocardial infraction incurs when an area of the heart is deprived of blood and therefore oxygen. After the death of cardiac tissue, the tissue is replaced with scar tissue. At the border between the scar tissue and the normal endocardium, there is a mixture of normal cells and scar tissue. Normal endocardium is comprised mainly of cardiac muscle cells. Infarcted myocardium is comprised mainly of protein strands without cells. The infarction border zone represents a gradual transition in tissue protein strand content. It is the protein strand content which causes the differences in impedance between normal, infarction and infarction border zone. Infarction border zone is an area of endocardium which often generates arrhythmias such as ventricular tachycardia.

It is the infarction border zone which is desired to be located for the purposes of ablation.

In accordance with the method of the present invention, it has been found that areas of normal tissue, infarcted tissue and areas immediately adjacent infarcted tissue, referred to herein as the infarction border zone may be identified or located within a beating heart by measuring the impedance of the endocardium at various points. It has been found in accordance with the method of the present invention that the three types of myocardial tissue namely normal, infarcted and infarction border zone tissue, present distinct ranges of impedance when measured in accordance with the methods of the present invention. It has been found that there is substantially a two fold increase in the impedance values of normal tissue as contrasted to infarcted tissue. Further, there is approximately a one fold increase in the infarction border zone as compared to infarcted tissue.

Although not limited to the locating of arrhythmias arising in the ventricles, the present invention is particularly useful for locating the source of such ventricular tachycardias. Further, in accordance with the present invention, once such potential source of arrhythmia, namely the infarction border zone, has been located, it may be ablated in accordance with the methods of the present invention utilizing the same catheter tip by the application of suitable amounts of RF energy, thereby reducing or eliminating the risk of arrhythmias such as ventricular tachycardias.

Figure 1:
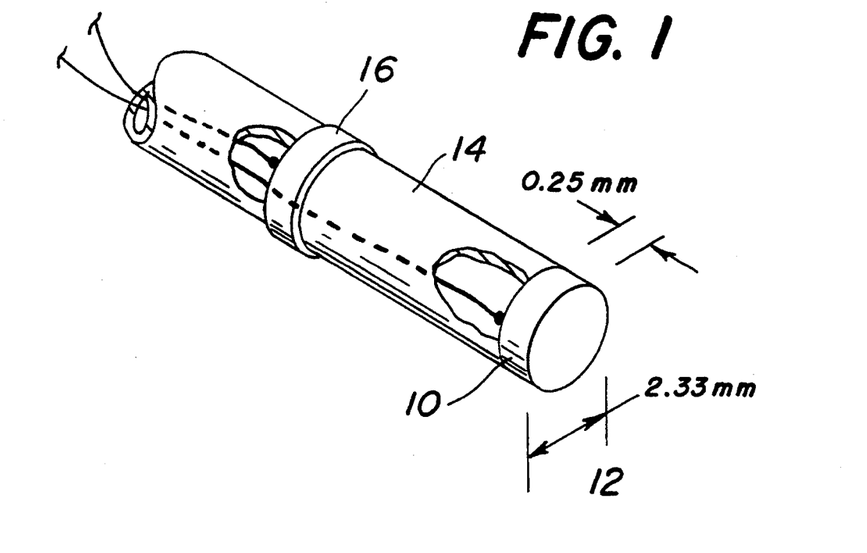
FIG. 1 is a view in perspective of a catheter tip which may be utilized in practicing the method of the present invention.

In accordance with the present invention, a catheter tip such as that shown in FIG. 1 may be utilized, although various other types of catheter tips may be utilized in practicing the method of the present invention. In accordance with the method of the present invention, it has been found to be advantageous to have a catheter tip design which comes directly into contact with the endocardium in such a manner as to reduce contact of the measuring tip with the blood in the beating heart, thereby enabling direct measurement of the impedance of the endocardium, as contrasted to the impedance of blood which is of a significantly lower value. An important concept in the technique of utilizing electrodes for assessing the adequacy of tissue contact is that the electrode be configured in such a way as to permit contact solely with the tissue of interest. The impedance value obtained by the electrode will then reflect the impedance of the contacted tissue only. Partial contact with tissue will render an ambiguous impedance value. It is further preferred that the catheter tip have heat dissipating design features for more accurate readings.

One suitable electrode for a catheter tip is illustrated in FIG. 1 wherein the tip is provided with a disc shape 10 which is provided with a predetermined significant depth which enhances heat dissipation. In the one example illustrated in FIG. 1, the disc shaped catheter may preferably have dimensions of a diameter 12 of 2.33 mm and a depth of 0.25 mm. However, it is understood that other dimensions of catheter tips may be utilized in practicing the method of the present invention. The catheter shaft 14 is preferably fitted with a recording electrode 16 which acts as a second electrode four recording purposes, such as recording local electrograms. The catheter utilized herein may be provided with one or more other electrodes so that various electrograms may be measured. Electrograms may also be measured with the impedance measurement electrode. Adequate recording of electrograms does not require sole contact of an electrode with the endocardial area of interest.

Figure 3:
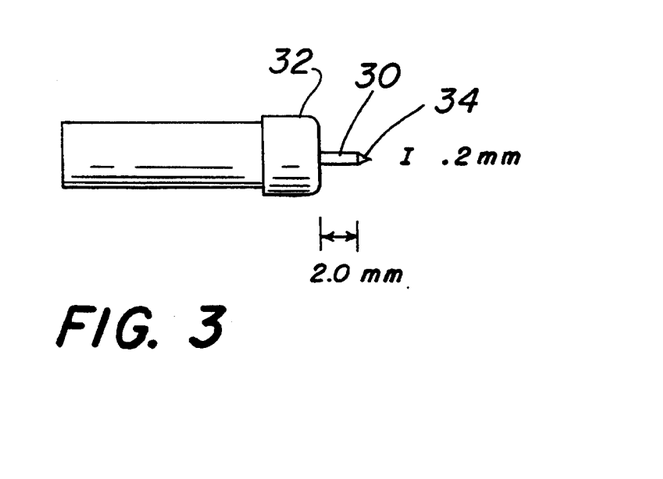
FIG. 3 is an elevation view of an alternate embodiment of a catheter tip which may be utilized in practicing the method of the present invention.

Referring to FIG. 3, there is shown another embodiment of an electrode 30 mounted on a catheter tip 32 which may be utilized in practicing the present invention. Catheter tip shown in FIG. 3 is provided with a sharp tip 34 and is relatively long, being 2 millimeters long and of a relatively small diameter, approximately 0.2 millimeters. The electrode 30 may be utilized to achieve exclusive tissue contact at odd angles. It will be apparent to those skilled in the art that various dimensions and modifications may be made to the electrodes for the catheter tips in accordance with the present invention.

As will be described more fully hereinafter, contact of such an electrode with the endocardium will provide a much higher impedance value than contact with the surrounding blood, thereby providing a means of endocardial contact assessment. The impedance difference between the endocardium and the blood depends on the surface area of the electrode, smaller surface areas record larger differences.

In practicing the method of the present invention, the catheter tip is used for both measuring impedance and ablating tissue. Tissue is ablated by the application of RF energy in suitable amounts, as is well known in the electrode catheterization art. The catheter may be guided to any chamber or area of the heart. In practicing the method of the present invention, the measuring electrode may be mounted in any way that allows direct contact with the endocardium. For example, left ventricular endocardial mapping may be performed by percutaneous insertion of the catheter into the femoral artery using the Seldinger technique, then retrograde passage of the catheter via the aorta and into the ventricle after crossing the aortic valve. Of course, access to any endocardial site in either atria or either ventricle may be achieved. In addition, mapping of the epicardium may be performed by thoracotomy and direct application of the electrode to the heart. The guidance of catheters into the heart, often using fluoroscopy, is known as cardiac catheterization, and is well known to those skilled in the art and need not be described here in detail.

Once the catheter tip is located in the appropriate chamber of the heart, the catheter tip may be manipulated to engage the myocardial area of interest with an appropriate contact pressure to achieve sole tissue contact to allow accurate measurement of the impedance at various locations. Utilization of the rendered impedance value may be performed using normal values based on research on subjects with normal hearts, and/or by using the impedance values measured in clearly normal areas of the heart of the subject undergoing investigation. By comparing values in these ways, areas of infarction or infarction bordering endocardium may be discerned. In this manner, suitable sites for application of energy for the performance of catheter ablation may be determined. Adequacy of electrode-tissue contact may be assessed as described hereinafter.

Figure 2:
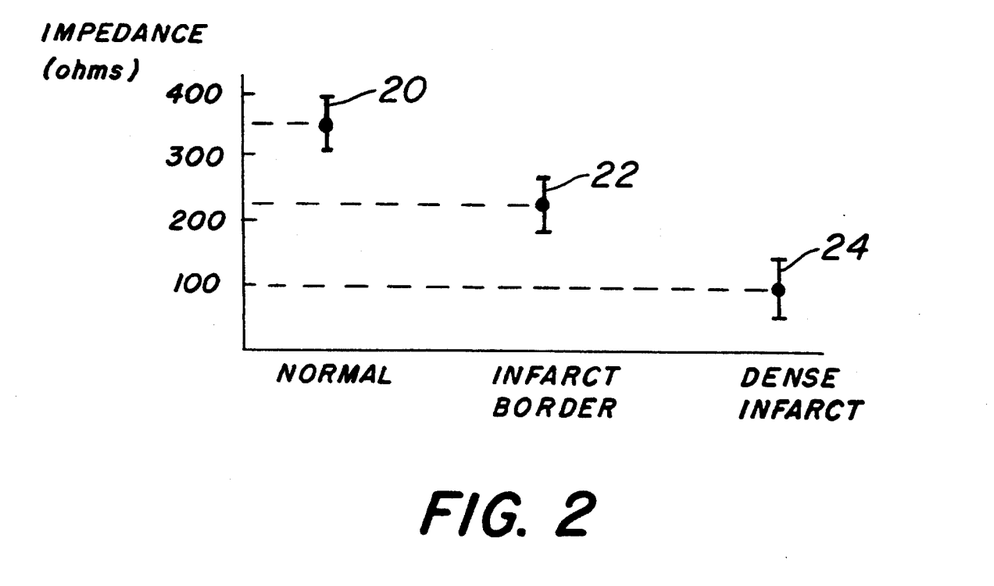
FIG. 2 is a graph of impedance values illustrative of the principles of the method of the present invention.

Ranges of impedance may be predetermined for normal endocardium, densely infarcted endocardium and infarction border zone endocardium as illustrated in FIG. 2. FIG. 2 illustrates specific values for normal, infarcted and infarction border zone endocardium measured in a significant number of sheep measured at 550 kHz. As illustrated in FIG. 2 at 20, normal endocardium tissue has an impedance range as illustrated with a mean in the neighborhood of 350 ohms. Endocardium in the infarction border zone has an impedance range as illustrated at 22 with a mean value of about 250 ohms. Densely infarcted endocardium has a tissue range as illustrated at 24 with a mean value of about 100 ohms. Generally, impedance values measured on infarcted endocardium were approximately 25% of those in normal endocardium and impedance values from infarction border areas were approximately 60–70% of those in normal endocardium. Although specific values may vary by electrode tip and the like, easily discernable differences in impedance are reproducibly achieved between normal, infarction border zone and infarcted endocardium.

In this manner, by comparing values measured at various points within the endocardium, infarcted tissue may be determined. Furthermore, normal tissue may be determined and most importantly, the infarction border zone may be determined. The infarction border zone has been determined to be a frequent source of arrhythmias, particularly of ventricular tachycardia. Accordingly, by use of the method of the present invention, sites for ablation within a beating heart may be determined utilizing cardiac catheterization techniques, and such sources of potential arrhythmias may be ablated, thereby reducing or eliminating the risk of arrhythmia, and particularly of ventricular tachycardia.

The method of determining the tissue to be ablated described herein is not limited to cardiac catheterization ablation for purposes of eliminating arrhythmiogenic sites. The method of the present invention may be utilized to measure impedances within various organs or body cavities to detect differences in tissue impedance to enable a determination as to a site to be ablated. For example, a tumor in the liver or bladder may be located by the detection of different impedance values between normal and tumor tissue, thereby enabling the ablation of such tumor tissue. The method of the present invention may be utilized to detect various different conditions in tissue which are accompanied by a change in impedance values.

In accordance with the method of the present invention, assessment of adequate contact between the electrode on the catheter tip and tissue in a fluid filled cavity or organ may be assessed. In a preferred application of practicing the method of the present invention, adequacy of electrode-endocardium contact may be assessed in a blood filled pumping heart. It has been found that there is significant impedance difference between the impedance of blood and endocardium tissue. This difference is very pronounced between blood and normal endocardium tissue. However, even with respect to infarcted endocardium, the impedance of the blood is characteristically measured at ranges approximately 25% less than the values achieved for infarcted tissue. This 25% change in impedance may be used to make the determination or alternatively specific values may be obtained for each patient by making an impedance measurement in the blood, preferably in a vessel, such as the aorta, outside of the heart, and another impedance measurement when the electrode is in direct stable placement with the endocardium as determined visually using fluoroscopy. Accordingly, by noting or monitoring the values of measured impedance, an assessment may be made as to whether there is adequate contact between the catheter tip electrode and the endocardium.

When radiofrequency energy is passed through an electrode which is in contact with the inside of the heart (endocardium), the volume of the endocardium which is in contact with the electrode will heat. If the tissue gets hot enough, it will die. If the tissue which is killed was part of an aberrant electrical circuit, such as those which cause cardiac arrhythmias, the arrhythmia will be cured. If the contact between the electrode and the endocardium is poor, the radiofrequency energy is quickly dissipated in the blood passing through the heart, and no significant accumulation of heat is achieved in the endocardium. Accordingly, the foregoing method of assessing adequate contact between the electrode and the endocardium is of great importance.

This method of assessing the adequacy of electrode-tissue contact may be utilized in any body cavity or organ which has a direct blood or other fluid (e.g. cerebrospinal fluid) interface.

Further, even if the contact is adequate, it is important to determine that the RF energy applied via the electrode mounted on the catheter tip is causing sufficient heating of the endocardium to allow for successful ablation. Should the endocardium be heated only to a lower temperature at which it can survive and return to normal function, if this tissue were a critical part of the propagation path of an arrhythmia, it is possible that the arrhythmia which was thought to be permanently eradicated during a given catheter ablation procedure may be only temporarily damaged. Unexpected recurrence of arrhythmias may lead to dangerous symptoms, including death in some cases and to morbidity, expense and risk of repeated hospitalization and further procedures. Accordingly, it is important to be able to determine during and immediately after the ablation process that the target endocardium to be ablated was sufficiently heated so as to sufficiently ablate the particular area of endocardium to prevent further arrhythmia generation.

In accordance with the present invention, it has been found that actual heating of the myocardium during the application of RF energy is associated with a reproducible linear change in the impedance of the myocardium. See FIG. 4. Since heating by the application of RF energy causes the ablation, it is important that the degree of heating of the endocardium or other tissue to be ablated be determined. Sufficient heating of the endocardium is capable of curing an arrhythmia resulting from that tissue. A temperature of approximately 50 degrees centigrade is required to successfully ablate myocardium. It is possible for endocardium which is heated to lower temperatures to survive and return to normal function.

In order to assess or monitor the heating of the endocardium, the impedance of the endocardium may be monitored during the application of the RF energy and/or immediately after the application of the RF energy. These impedance measurements are compared to a base line impedance value established by measuring the impedance in or around the area to be ablated at normal body temperature, preferably, but not necessarily, immediately before the application of the RF energy for ablation. Once a consistent measurement of impedance is obtained in the base line state, radiofrequency energy or other ablation energy is applied. As the myocardium located at the surface of the electrode heats, local impedance changes, and such changes may be continuously measured via the energy delivering electrode.

In practicing the method of assessing the degree of heating during the ablation process, as well as in the electrode-tissue contact assessment, it is preferable to use a catheter electrode such as that shown in FIG. 1 although other types of electrodes may be utilized in practicing the method the present invention so long as the design criteria outlined above are taken into account.

Figure 4:
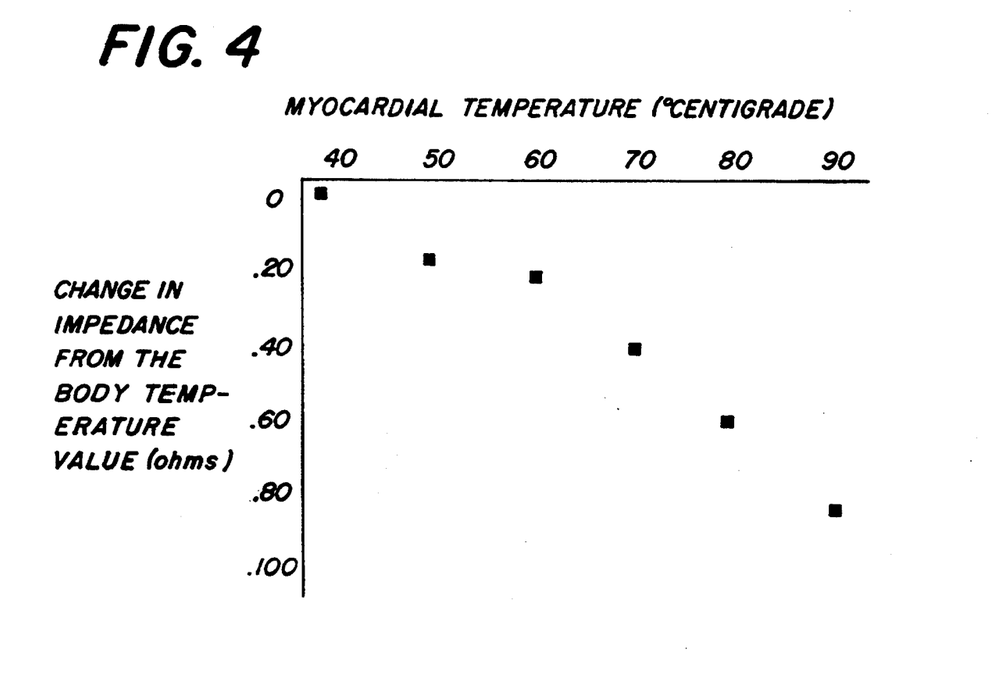
FIG. 4 is a graph of decreasing impedance values with increasing temperature of tissue being ablated in accordance with the method of the present invention.

FIG. 4 is illustrative of the relationship between increasing tissue temperature and decreasing impedance. FIG. 4 illustrates data obtained using the electrode of FIG. 1 on the epicardium of live pigs, measured in unipolar fashion at 550 kilohertz. A substantially linear decrease in impedance was shown in association with rising tissue temperature at the electrode surface induced by the application of RF energy. This pattern was highly reproducible. Accordingly, the tissue impedance monitoring provides reliable information of tissue temperature at the site of energy application via the electrode. It is believed that this is the only unequivocal evidence of actual tissue heating.

Although the data is reproducible and values may be established in which absolute impedance measurement correlate with a predetermined amount of tissue heating, in the preferred method of practicing the invention, each patient's impedance values at body temperature, before application of energy may be used to establish the base line. In this way, each patient acts as his/her own standard of reference, from which the degree of tissue heating may be judged from the amount of tissue impedance decrease with each energy application.

Numerous variations may be made in practicing the methods of the present invention without departing from the spirit or scope of the present invention. Various frequencies may be utilized in the measuring process ranging from 1 kilohertz to 1 megahertz. It has been found that by using frequencies at less than 100 kilohertz, better resolution of impedance values is obtained for demonstrating tissue heating. In the preferred method of practicing the invention, impedance has been measured at frequencies at which RF energy is applied through commercially available devices, namely in the 500 to 750 kilohertz range. Although larger differences in ranges of impedance values between normal, infarction border and infarcted tissues are found at lower frequencies, frequencies utilized may be up into the megahertz range. However, preferably the frequency used is less than 1,000 kHz. In a preferred method of practicing the invention to date, impedance measurements have been made at 550 kHz. At lower frequency ranges, particularly in the 1 kHz range, although the largest differences between ranges of impedance values for normal, infarcted and infarction border zone tissue are observed, electrode polarization artifacts may present a serious problem. However, as referred to above, various other types of catheter tips may be utilized, including a catheter tip having four spaced electrodes mounted in an insulative base. A fixed current may be passed through endocardium between the two outer electrodes and the voltage developed in the endocardium between the two inner electrodes may be measured. The impedance may be readily calculated by the equipment as the ratio of voltage to current. Typically, a small subthreshold current of approximately 15 microamperes alternating current may be utilized for this purpose.

It is further noted that the methods described and illustrated herein are not limited to use in the myocardium. The impedance measuring method to determine differences in tissue, the method of determining whether the electrode is in contact with the tissue and the method of assessing adequate ablation of undesired tissue may be used in various applications in the body, including, but not limited to ablation of tumors, cancerous or benign, or the like.

In view of the above, the present invention may be embodied in other specific forms without departing from the spirit or essential attributes thereof and, accordingly, reference should be made to the appended claims, rather than to the foregoing specification as indicating the scope of the invention.

We claim:

1. A method of locating a source of arrhythmia in a beating heart, comprising:

inserting an impedance measuring electrode of a catheter into a chamber of a beating heart;

measuring impedance of endocardium at various locations within the chamber of the beating heart using said electrode of said catheter; and determining a border zone between normal and infarcted endocardium based upon measured impedance, said border zone being said source.

2. A method in accordance with claim 1, wherein inserting step includes inserting said measuring electrode of said catheter into a left ventricle of the beating heart.

3. A method in accordance with claim 1, wherein inserting step includes inserting said measuring electrode of said catheter into a right ventricle of the beating heart.

4. A method of locating a source of arrythmia and reducing the risk of future arrythmia in a beating heart, comprising:

inserting an electrode of a catheter into a chamber of a beating heart, said electrode being adapted for impedance measuring and ablation;

measuring impedance of endocardium at various locations within the chamber of the beating heart using said electrode of said catheter;

determining a border zone between normal and infarcted endocardium based upon measured impedance; and using said electrode of said catheter to ablate endocardium in said border zone.

5. A method in accordance with claim 4, wherein inserting step includes inserting said electrode of said catheter into a left ventricle of a beating heart.

6. A method in accordance with claim 4, wherein inserting step includes inserting said electrode of said catheter into a right ventricle of the beating heart.

7. A method of locating a source of arrythmia and infarcted myocardial tissue in a beating heart, comprising:

inserting an impedance measuring electrode of a catheter into a chamber of a beating heart;

measuring impedance of endocardium at various locations within the chamber of the beating heart using said electrode of said catheter; and comparing the measured impedance values with predetermined ranges of values to identify an infarcted area and an infarct border area of myocardium and distinguishing such areas from normal myocardium.

8. A method in accordance with claim 7, wherein inserting step includes inserting said measuring electrode of said catheter into a left ventricle of the beating heart.

9. A method in accordance with claim 7, wherein inserting step includes inserting said impedance measuring electrode of said catheter into a right ventricle of the beating heart.

10. A method in accordance with claim 1 wherein said step of determining a border zone between normal and infarcted endocardium includes the step of determining three predetermined ranges of impedance values, a highest range of impedance values being normal endocardium, a lowest range of impedance values representing infarcted endocardium and a middle range of impedance values representing said border zone and the source of arrythmia.

11. A method in accordance with claim 4 wherein said step of determining a border zone between normal and infarcted endocardium includes the step of determining three predetermined ranges of impedance values, a highest range of impedance values being normal endocardium, a lowest range of impedance values representing infarcted endocardium and a middle range of impedance values representing said border zone.

12. A method in accordance with claim 7, including the step of establishing predetermined ranges of values to identify an infarcted area and an infarct border area of myocardium.

13. A method in accordance with claim 12 wherein said step of establishing predetermined ranges of values includes the step of measuring the impedance of normal endocardium of a patient being treated and deriving from the normal endocardium impedance values ranges of impedance values for infarcted areas and infarct border areas.

14. A method in accordance with claim 12 wherein said step of establishing predetermined ranges of values to identify the infarcted area and the infarct border area include the step of performing impedance measurements of the endocardium in a plurality of beating hearts and recording ranges of the impedance values for future use.

15. A method of locating infarcted myocardial tissue in a beating heart, comprising:

inserting an impedance measuring electrode of a catheter into a chamber of a beating heart;

measuring impedance of endocardium at various locations within the chamber of the beating heart using said electrode of said catheter; and comparing measured impedance values with a predetermined range of values to identify an infarcted area of myocardium and distinguishing such area from normal myocardium.

16. A method of locating a border zone separating normal and infarcted myocardium, comprising:

inserting an impedance measuring electrode of a catheter into a chamber of a beating heart;

measuring impedance of endocardium at various locations within the chamber of the beating heart using said electrode of said catheter; and comparing measured impedance values with a predetermined range of values to identify a border zone separating normal and infarcted myocardium and to distinguish such area from normal and infarcted myocardium.

* * * * *

UNITED STATES PATENT AND TRADEMARK OFFICE
CERTIFICATE OF CORRECTION

PATENT NO. : 5,447,529
DATED : September 5, 1995
INVENTOR(S) : Francis E. Marchlinski, et al.

It is certified that error appears in the above-indentified patent and that said Letters Patent is hereby corrected as shown below:

The title page, showing an illustrative figure, should be deleted and substitute therefor the attached title page.

Delete Figures 1-4 and substitute therefor the attached two sheets containing Figures 1-4.

Column 3, line 17, before "shown" insert --are--.

Column 9, line 31, delete the second occurrence of "a" and substitute therefor --the--.

Signed and Sealed this

Nineteenth Day of March, 1996

Attest:

BRUCE LEHMAN

*Attesting Officer*  *Commissioner of Patents and Trademarks*

United States Patent [19]

Marchlinski et al.

[11] Patent Number: 5,447,529
[45] Date of Patent: Sep. 5, 1995

[54] METHOD OF USING ENDOCARDIAL IMPEDANCE FOR DETERMINING ELECTRODE-TISSUE CONTACT, APPROPRIATE SITES FOR ARRHYTHMIA ABLATION AND TISSUE HEATING DURING ABLATION

[75] Inventors: Francis E. Marchlinski, Bala Cynwyd; David S. Schwartzman, Philadelphia, both of Pa.; Mark S. Mirotznik, Silver Spring, Md.; Kenneth R. Foster, Haverford, Pa.; Charles D. Gottlieb, Wynnewood, Pa.; Isaac Chang, Philadelphia, Pa.

[73] Assignees: Philadelphia Heart Institute; The Trustees of the University of Pennsylvania, both of Philadelphia, Pa.; Catholic University of America, Washington, D.C.

[21] Appl. No.: 188,514

[22] Filed: Jan. 28, 1994

[51] Int. Cl.6 .................. A61B 17/39; A61N 1/05
[52] U.S. Cl. ........................... 607/99; 128/739; 128/642; 128/695 R; 128/713; 607/122
[58] Field of Search ............... 128/637, 642, 662.06, 128/670, 692, 701, 713, 654, 672, 695 R, 734, 693; 606/41; 607/41, 99

[56] References Cited

U.S. PATENT DOCUMENTS

| | | | |
|---|---|---|---|
| 4,380,237 | 4/1983 | Newbower | 128/693 |
| 4,674,518 | 6/1987 | Salo | 128/695 |
| 4,852,580 | 8/1989 | Wood | 128/693 |
| 5,058,583 | 10/1991 | Geddes et al. | 128/419 |
| 5,092,339 | 3/1992 | Geddes et al. | 128/692 |
| 5,195,968 | 3/1993 | Lundquist et al. | 604/95 |
| 5,197,467 | 3/1993 | Steinhaus et al. | 128/419 |
| 5,224,475 | 7/1993 | Berg et al. | 128/419 |
| 5,239,999 | 8/1993 | Imran | 128/642 |
| 5,246,008 | 9/1993 | Mueller | 128/695 |
| 5,282,840 | 2/1994 | Hudrlik | 607/28 |
| 5,334,193 | 8/1994 | Nardella | 606/41 |
| 5,341,807 | 8/1994 | Nardella | 606/41 |

OTHER PUBLICATIONS

Myocardial Electrical Impedance Mapping of Ischemic Sheep Hearts and Healing Aneurysms–Circulation, vol. 87, pp. 188–207 (1993).

*Primary Examiner*—Lee S. Cohen
*Assistant Examiner*—Stephen Huang
*Attorney, Agent, or Firm*—Michael F. Petock

[57] ABSTRACT

A method of locating infarcted myocardial tissue in a beating heart includes the step of inserting an impedance measuring tip of a catheter into the chamber of the beating heart, particularly the left or right ventricle, and measuring the impedance of the endocardium at various locations within the chamber of the beating heart. The values measured are compared to impedance values with a predetermined range of values to identify an infarcted area of myocardium and distinguish such area from normal myocardium. The measurements are also compared to a range of values for an infarction border zone. In accordance with the invention, the infarction border zone may be located. The infarction border zone is a significant source of arrhythmia, and particularly of ventricular tachycardia. Further, in accordance with the methods of the present invention, the risk of arrhythmia in a beating heart may be substantially reduced or eliminated by ablating endocardium within the infarction border zone utilizing the same catheter tip. Impedance measurements may also be utilized to assess the adequacy of the electrode-tissue contact, particularly in a fluid filled body organ or cavity. Further, the effectiveness of the ablation of the tissue may be determined by determining the degree of heating of the tissue by measuring the change in impedance in the area of ablation.

16 Claims, 2 Drawing Sheets

UNITED STATES PATENT AND TRADEMARK OFFICE
CERTIFICATE OF CORRECTION

PATENT NO. : 5,447,529

DATED : September 5, 1995

INVENTOR(S) : Marchlinski et al.

It is certified that error appears in the above-identified patent and that said Letters Patent is hereby corrected as shown below:

On the title page, item [75],
                          delete "Gottleb" and insert therefor --Gottlieb--.

Signed and Sealed this

Twenty-eighth Day of May, 1996

Attest:

BRUCE LEHMAN

*Attesting Officer*        *Commissioner of Patents and Trademarks*